US012763220B2

(12) United States Patent
Suita et al.

(10) Patent No.: US 12,763,220 B2
(45) Date of Patent: Oct. 13, 2026

(54) INJURY ESTIMATION SYSTEM, INJURY ESTIMATION METHOD, AND INJURY ESTIMATION PROGRAM

(71) Applicant: TOYOTA JIDOSHA KABUSHIKI KAISHA, Toyota (JP)

(72) Inventors: Kazutsugu Suita, Nagoya (JP); Nobuyuki Yasui, Okazaki (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 1066 days.

(21) Appl. No.: 17/876,098

(22) Filed: Jul. 28, 2022

(65) Prior Publication Data

US 2023/0072522 A1 Mar. 9, 2023

(30) Foreign Application Priority Data

Sep. 7, 2021 (JP) ................................ 2021-145741

(51) Int. Cl.
*G16H 50/50* (2018.01)

(52) U.S. Cl.
CPC .................................. *G16H 50/50* (2018.01)

(58) Field of Classification Search
USPC ........................................................ 600/567
See application file for complete search history.

(56) References Cited

U.S. PATENT DOCUMENTS

2002/0016700 A1 2/2002 Furusu et al.
2014/0276230 A1* 9/2014 Pattison ............... A61B 5/0051 600/587
2018/0285516 A1* 10/2018 Shah ....................... G06F 17/16
2019/0172585 A1* 6/2019 Mazumder ............ G16H 50/30

FOREIGN PATENT DOCUMENTS

JP 2005-353078 A 12/2005
JP 2011-70301 A 4/2011
JP 2020-61088 A 4/2020
WO 2007/019546 A2 2/2007

* cited by examiner

*Primary Examiner* — Aurelie H Tu
(74) *Attorney, Agent, or Firm* — Sughrue Mion, PLLC

(57) ABSTRACT

An injury estimation system according to the embodiment is for estimating an injury to a human body by using a human body model and a contact object model including a database configured to store, in association with each other, human body information, contact object information, and injury information, a human body model generation unit configured to generate the human body model, a contact object model generation unit configured to generate the contact object model, a reproduction unit configured to reproduce a result of an injury to the human body, a correction unit configured to correct the human body model and the contact object model based on the reproduced injury information and the injury information about the human body stored in the database, and an estimation unit configured to estimate the injury to the human body by using the corrected human body model and the corrected contact object model.

7 Claims, 4 Drawing Sheets

INJURY ESTIMATION SYSTEM, INJURY ESTIMATION METHOD, AND INJURY ESTIMATION PROGRAM

CROSS REFERENCE TO RELATED APPLICATIONS

This application is based upon and claims the benefit of priority from Japanese patent application No. 2021-145741, filed on Sep. 7, 2021, the disclosure of which is incorporated herein in its entirety by reference.

BACKGROUND

The present disclosure relates to an injury estimation system, an injury estimation method, and an injury estimation program.

Japanese Unexamined Patent Application Publication No. 2011-070301 discloses a technique for assessing the degree of harm to a human body in a situation that may occur during the use of equipment by focusing on a maximum value of an impact load when a human body model collides with the equipment.

SUMMARY

The method disclosed in Japanese Unexamined Patent Application Publication No. 2011-070301 described above assesses the degree of harm based on the impact load. On the other hand, since the degree of harm may depend on factors other than the impact load, a more accurate assessment method has been required.

An object of the present disclosure is to provide an injury estimation system, an injury estimation method, and an injury estimation program capable of improving accuracy in estimation of an injury to the human body.

In an example aspect of the present disclosure, an injury estimation system for estimating an injury to a human body by using a human body model and a contact object model includes:

a database configured to store, in association with each other, human body information about a human body, contact object information about a contact object, and injury information about an injury to the human body generated in contact between the human body and the contact object;

a human body model generation unit configured to generate the human body model by using the human body information stored in the database;

a contact object model generation unit configured to generate a contact object model by using the contact object information stored in the database;

a reproduction unit configured to reproduce a result of an injury to the human body by using the human body model and the contact object model;

a correction unit configured to correct the human body model and the contact object model based on the reproduced injury information indicated by the result of the injury to the human body and the injury information about the human body stored in the database; and an estimation unit configured to estimate the injury to the human body by using the corrected human body model and the corrected contact object model.

In another example aspect of the present disclosure, an injury estimation method for estimating an injury to a human body by using a human body model and a contact object model includes:

generating the human body model by using human body information stored in a database configured to store, in association with each other, the human body information about a human body, contact object information about a contact object, and injury information about an injury to the human body generated in contact between the human body and the contact object;

generating the contact object model by using the contact object information stored in the database;

reproducing a result of an injury to the human body by using the human body model and the contact object model;

correcting the human body model and the contact object model based on the reproduced injury information indicated by the result of the injury to the human body and the injury information about the human body stored in the database; and estimating the injury to the human body by using the corrected human body model and the corrected contact object model.

In another example aspect of the present disclosure, an injury estimation program for estimating an injury to a human body by using a human body model and a contact object model for causing a computer to execute:

generating the human body model by using human body information stored in a database configured to store, in association with each other, the human body information about a human body, contact object information about a contact object, and injury information about an injury to the human body generated in contact between the human body and the contact object;

generating the contact object model by using the contact object information stored in the database;

reproducing a result of an injury to the human body by using the human body model and the contact object model;

correcting the human body model and the contact object model based on the reproduced injury information indicated by the result of the injury to the human body and the injury information about the human body stored in the database; and estimating the injury to the human body by using the corrected human body model and the corrected contact object model.

According to the present disclosure, it is possible to provide an injury estimation system, an injury estimation method, and an injury estimation program capable of improving accuracy in estimation of an injury to the human body.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Hereinafter, specific embodiments to which the present disclosure is applied will be described in detail with reference to the drawings. However, the present disclosure is not limited to the following embodiments. In order to clarify the description, the following description and drawings have been appropriately simplified.

First Embodiment

Figure 1:
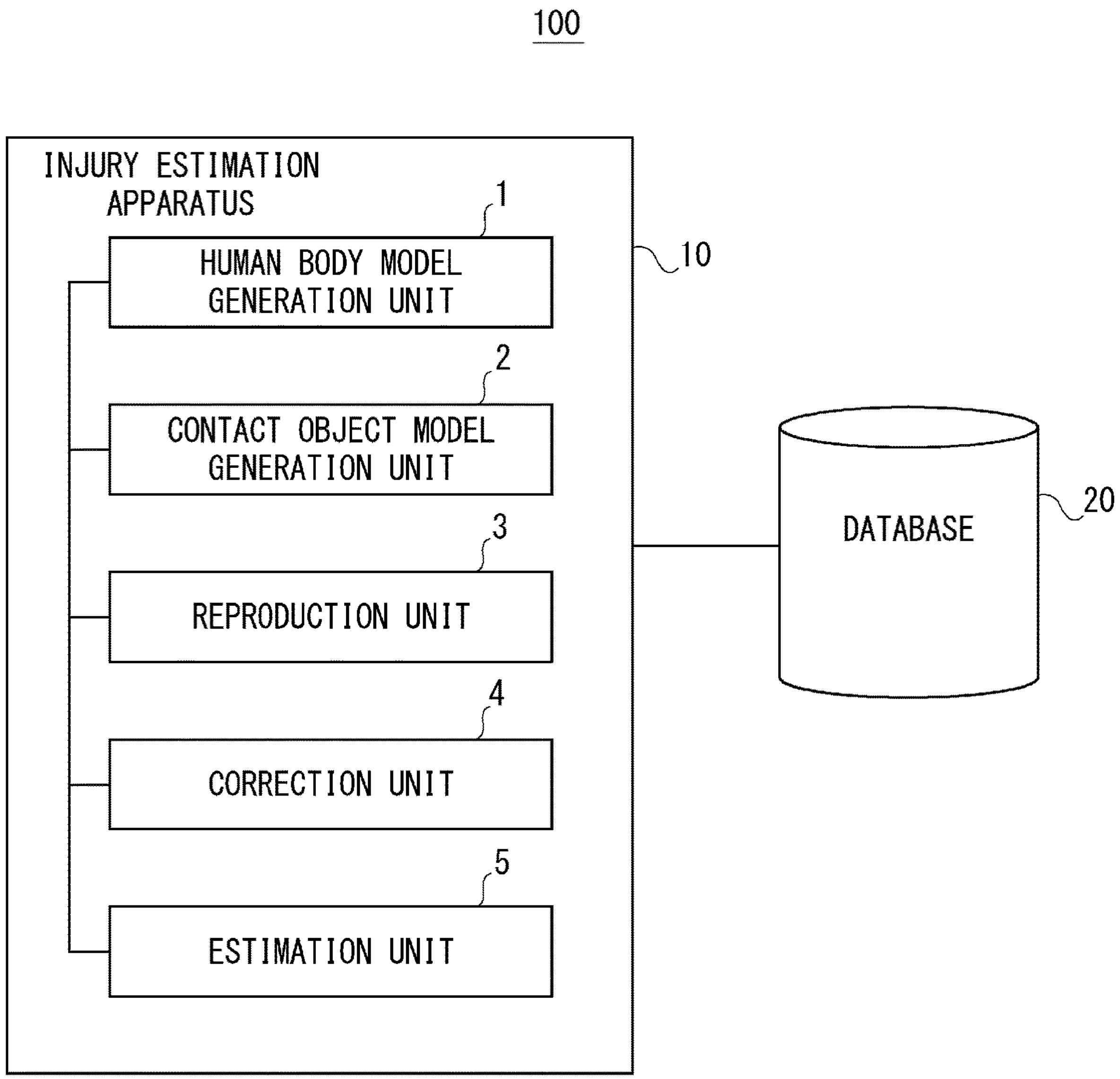
FIG. 1 is a block diagram showing a configuration of an injury estimation system according to a first embodiment.

An injury estimation system 100 according to a first embodiment will be described with reference to FIG. 1. As shown in FIG. 1, the injury estimation system 100 includes an injury estimation apparatus 10 and a database 20. The injury estimation apparatus 10 is connected to the database 20. The injury estimation apparatus 10 includes a human body model generation unit 1, a contact object model generation unit 2, a reproduction unit 3, a correction unit 4, and an estimation unit 5.

The injury estimation system 100 estimates an injury to a human body by using a human body model and a contact object model. The contact object may be, for example, a nail, a saw, a press, etc. The contact object is not limited to them, and may be any object. The injury estimated by the injury estimation system 100 may be a specific symptom or disease name, such as, a blister, internal bleeding, muscle tear, contusion, or fracture in a human body, or may be information about various parameters constituting the injury.

The injury estimation apparatus 10 is, for example, a computer apparatus. The human body model and the contact object model described above are modeled on a computer by the injury estimation apparatus 10. That is, the injury estimation system 100 uses the injury estimation apparatus 10 to simulate contact between a human body model and a contact object model on a computer to estimate the injury to the human body when the human body comes into contact with the contact object.

In the injury estimation system 100, the precision of the human body model and the contact object model can be improved by correcting the human body model and the contact object model based on past injury information. Thus, the injury estimation system 100 can improve the accuracy in the estimation of injuries to the human body.

The database 20 stores, in association with each other, human body information about the human body, contact object information about the contact object, and injury information of the human body generated due to the contact between the human body and the contact object. That is, the database 20 records the human body information, the contact object information, and the injury information when an injury to the human body occurs due to the contact between the human body and the contact object.

The database 20 may be provided inside the injury estimation apparatus 10 or may be provided outside the injury estimation apparatus 10 as shown in FIG. 1. The database 20 may be provided, for example, on a cloud.

The human body model generation unit 1 generates the human body model by using the human body information stored in the database 20. The human body model is generated in a virtual space on a computer by the human body model generation unit 1.

The human body information is information related to the characteristics of the human body and includes parameters necessary for modeling a human body. For example, the human body information is information such as age, gender, part, mass, elasticity, viscosity, etc., in the target human body.

For example, in general, the epidermis of a human body aged 0 to 10 years is softer than that of a human body aged 50 to 60 years. That is, for example, age can be used as a parameter of the human body model, because the characteristics of the human body change with age. Specifically, as age increases, the parameter indicating the elasticity of the human body model may be changed to become more highly elastic. Similarly, as age decreases, the parameter indicating the elasticity of the human body model may be changed to become less elastic.

In general, men have more muscle mass than women. That is, gender can be used as a parameter of the human body model. Specifically, a male human body model may have a parameter indicating higher elasticity than that of a female human body model.

As described above, the human body model generation unit 1 can improve the precision of the human body model to be generated by adjusting various parameters in consideration of the characteristics of the target human body.

The contact object information is information about the characteristics of the contact object and includes parameters necessary to model the contact object. For example, the contact object information includes information about a shape, a material property, and the like of the contact object. The material property of the contact object is, for example, the mass, elasticity, viscosity or the like of the contact object.

The injury information includes, for example, information about a shape, contact area, or an amount of chamfer of a contact region of the human body which comes into contact with the contact object. Note that the injury information is not limited to these, and may include other parameters, specific symptoms, and disease names.

Further, in the database 20, for example, information about a speed and an acceleration when the human body comes into contact with the contact object, and information about a contact angle at which the human body comes into contact with the contact object may be recorded from the state of the injury caused by the contact between the human body and the contact object. These pieces of information about situations of the contact can be used as contact conditions to reproduce the contact between the human body model and the contact object model.

The human body model may include a living body model related to a living body of a human and a protective equipment model related to protective equipment attached to the living body. The human body model generation unit 1 can generate the living body model by using parameters such as age, gender, part, mass, elasticity, and viscosity in the same manner as the human body model.

For example, when the living body model is a living body model of a hand of a human body, it is preferable that the living body model include parameters related to a frictional force in the surface layer of the hand of the human body, slipperiness in the surface layer of the hand of the human body, fat amount in the hand of the human body, a muscle mass in the hand of the human body, or bone in the hand of the human body in order to improve the accuracy of the living body model. That is, the injury estimation system 100 can estimate an injury to the hand of the human body which has come into contact with the contact object more accurately by using the living body model having these parameters.

The protective equipment is an article used to protect a living body, such as a glove, a safety shoe, a face mask, and clothing including work clothes. The protective equipment information is information related to the characteristics of the protective equipment and includes parameters necessary for modeling the protective equipment. The protective equipment information is information such as mass, elasticity, viscosity, and the like. The human body model generation unit 1 can generate the protective equipment model by using the protective equipment information.

The protective equipment information may be recorded together with the human body information in the database 20, or may be separately recorded in a database for the protective equipment. These living body models and protective equipment models are generated in a virtual space on a computer by the human body model generation unit 1.

The contact object model generation unit 2 generates a contact object model by using the contact object information stored in the database 20. Like the human body model, the contact object model is also generated in a virtual space on a computer.

For example, if a tip of the contact object is pointed, the degree of an injury is increased. Further, for example, when the diameter of the contact object is small, the pressure on the human body increases, and the degree of the injury increases. Further, for example, when the material property of the contact object is light and soft, the degree of the injury is reduced. On the other hand, when the material property of the contact object is heavy and hard, the degree of the injury is large. That is, the contact object model preferably includes parameters related to the shape or material property of the contact object.

That is, the contact object model generation unit 2 generates the contact object model in consideration of the shape and the material property of the contact object, so that the accuracy of the contact object model can be enhanced.

The contact object model may include other parameters such as a parameter related to the temperature of the contact object.

The reproduction unit 3 reproduces a result of the injury to the human body by using the human body model and the contact object model. The reproduction unit 3 reproduces past results of the injury to the human body by bringing the human body model into contact with the contact object model under predetermined contact conditions such as a velocity, an acceleration, and a contact angle when the human body comes into contact with the contact object stored in the database 20 as described above.

The correction unit 4 corrects the human body model and the contact object model based on the injury information shown by the reproduced result of the injury to the human body and the injury information of the human body stored in the database 20. When the injury information shown by the reproduced result of the injury to the human body is different from the injury information of the human body stored in the database 20, the correction unit 4 corrects the human body model by changing the parameters of the human body model. Similarly, the correction unit 4 corrects the contact object model by changing the parameters of the contact object model.

That is, the correction unit 4 compares the injury information shown by the reproduced result of the injury to the human body with the past injury information, and corrects the human body model and the contact object model, thereby improving the precision and accuracy of the human body model and the contact object model.

When the human body model and the contact object model are corrected by the correction unit 4, the reproduction unit 3 may reproduce the result of the injury to the human body again by using the corrected human body model and the corrected contact object model. After that, the human body model and the contact object model may be corrected again by the correction unit 4. That is, the reproduction by the reproduction unit 3 and the correction by the correction unit 4 may be repeated until a difference between the injury information indicated by the reproduced result of the injury to the human body and the injury information of the human body stored in the database 20 falls within a predetermined range. The correction unit 4 may correct only the human body model or only the contact object model.

For example, the correction unit 4 may determine whether or not the correction is to be made based on whether or not a difference between the shape of the reproduced contact region of the human body and the shape of the contact region stored in the database 20 is within a predetermined range. When the difference between the shape of the reproduced contact region of the human body and the shape of the contact region stored in the database 20 is outside the predetermined range, the correction unit 4 corrects the human body model and the contact object model, while when the difference is within the predetermined range, the correction unit 4 does not correct the human body model and the contact object model.

Similarly, for example, the correction unit 4 may determine whether or not to correct the human body model and the contact object model according to whether or not the difference between the reproduced contact area of the human body which has come into contact with the contact object and the contact area stored in the database 20 is within the predetermined range. When the difference between the reproduced contact area of the human body and the contact area stored in the database 20 is outside the predetermined range, the correction unit 4 corrects the human body model and the contact object model, while when the difference is within the predetermined range, the correction unit 4 does not correct the human body model and the contact object model.

By correcting the human body model and the contact object model, the injury estimation apparatus 10 can generate an accurate human body model and an accurate contact object model, respectively, from which past injuries stored in the database 20 can be derived. The correction unit 4 may store the corrected human body model and the corrected contact object model in the database 20. In this case, the estimation unit 5, which will be described later, can refer to the database 20 and use the corresponding human body model and contact object model as desired.

The estimation unit 5 estimates the injury to the human body by using the corrected human body model and the corrected contact object model. The precision and accuracy of the human body model and the contact object model are improved by the correction unit 4. Therefore, the estimation unit 5 can estimate the injury to the human body by bringing the corrected human body model into contact with the corrected contact object model under a specified contact condition. Clearly, the combination of the human body model and the contact object model may be any combination, and the contact condition can be changed as desired.

The estimation unit 5 can estimate the injury to the human body by bringing the corrected human body model into contact with the corrected contact object model in a virtual space on a computer. The estimation unit 5 may be capable of displaying the estimated injury to the human body through a display unit (not shown). For example, the estimation unit 5 may display the injury to the human body as a 3D map on the display unit. The estimation unit 5 may notify a user of a specific symptom or disease name of the estimated injury to the human body.

Figure 2:
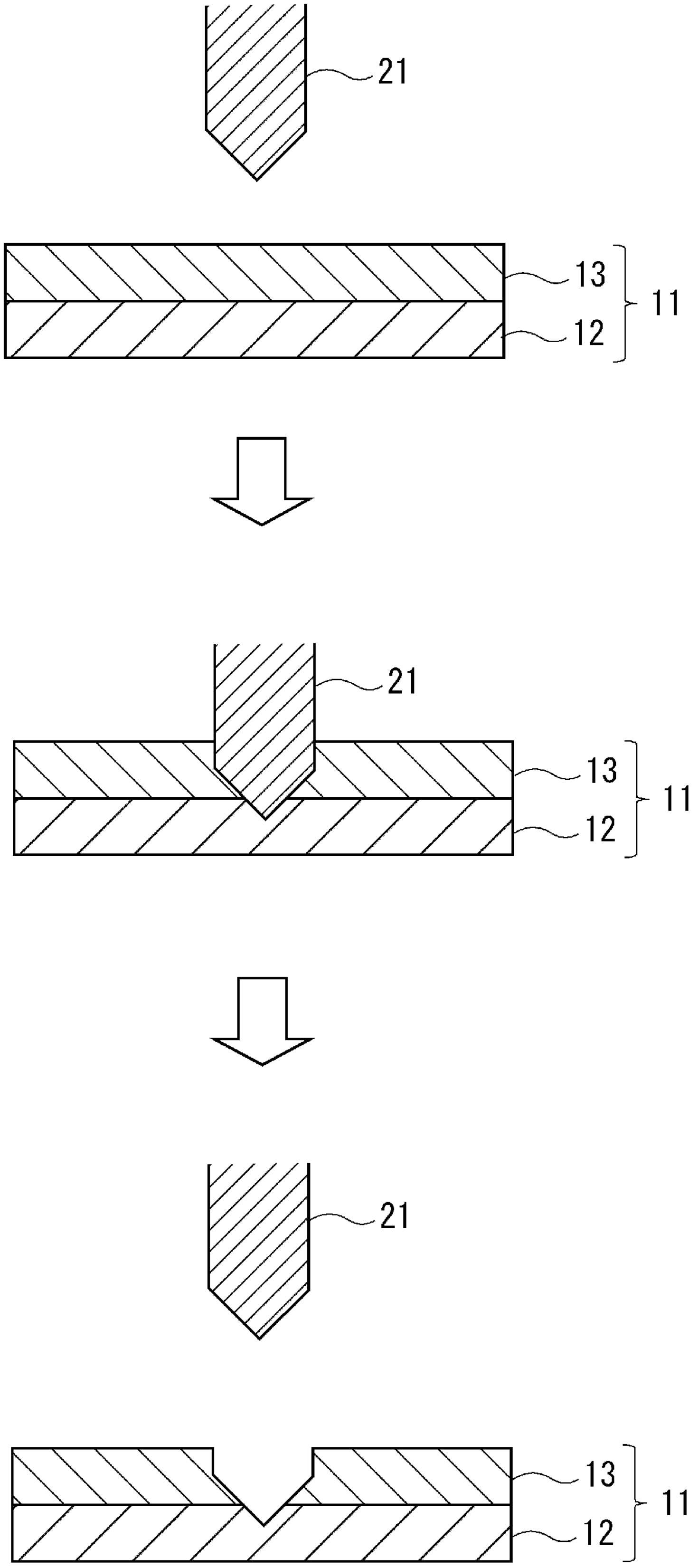
FIG. 2 is a cross-sectional view showing a state of contact between a human body model and a contact object model according to the first embodiment.

Referring now to FIG. 2, an overview of a method of reproducing an injury by the injury estimation system 100 and a method of estimating an injury will be described. FIG. 2 is a cross-sectional view showing a state of contact between a human body model 11 and a contact object model 21 according to the first embodiment.

In the upper view of FIG. 2, the human body model 11 and the contact object model 21 are shown. The human body model 11 is composed of a living body model 12 and a protective equipment model 13. The injury estimation apparatus 10 in the injury estimation system 100 brings the human body model 11 into contact with the contact object model 21 under predetermined contact conditions (FIG. 2). As a result, the injury estimation system 100 can reproduce the injury to the human body by using the human body model 11 and the contact object model 21 (the lower view of FIG. 2).

The injury estimation system 100 compares the injury information indicated by the reproduced result of the injury with the past injury information stored in the database 20, and corrects the human body model 11 and the contact object model 21 to thereby improve the precision of the human body model 11 and the contact object model 21.

Also, as shown in FIG. 2, the injury estimation system 100 can estimate the injury to the human body under a specified contact condition by bringing the modified human body model 11 into contact with the modified contact object model 21. That is, according to the injury estimation system 100 of this embodiment, the accuracy in the injury estimation of the human body can be improved.

At the work site, the risk of the injury to hands is particularly high among parts of a human body. The injury estimation system 100 according to this embodiment can also be suitably used for estimating injuries to a hand of a human body.

Further, the estimation unit 5 can, for example, estimate the injury to the human body when the human body comes into contact with the contact object in an area of 1 $cm^2$ or more on the surface of the human body by using the corrected human body model and the corrected contact object model. That is, the injury estimation system 100 according to this embodiment can also be suitably used to compare the degree of the injury to the human body in any combination of a human body and a contact object.

Figure 3:
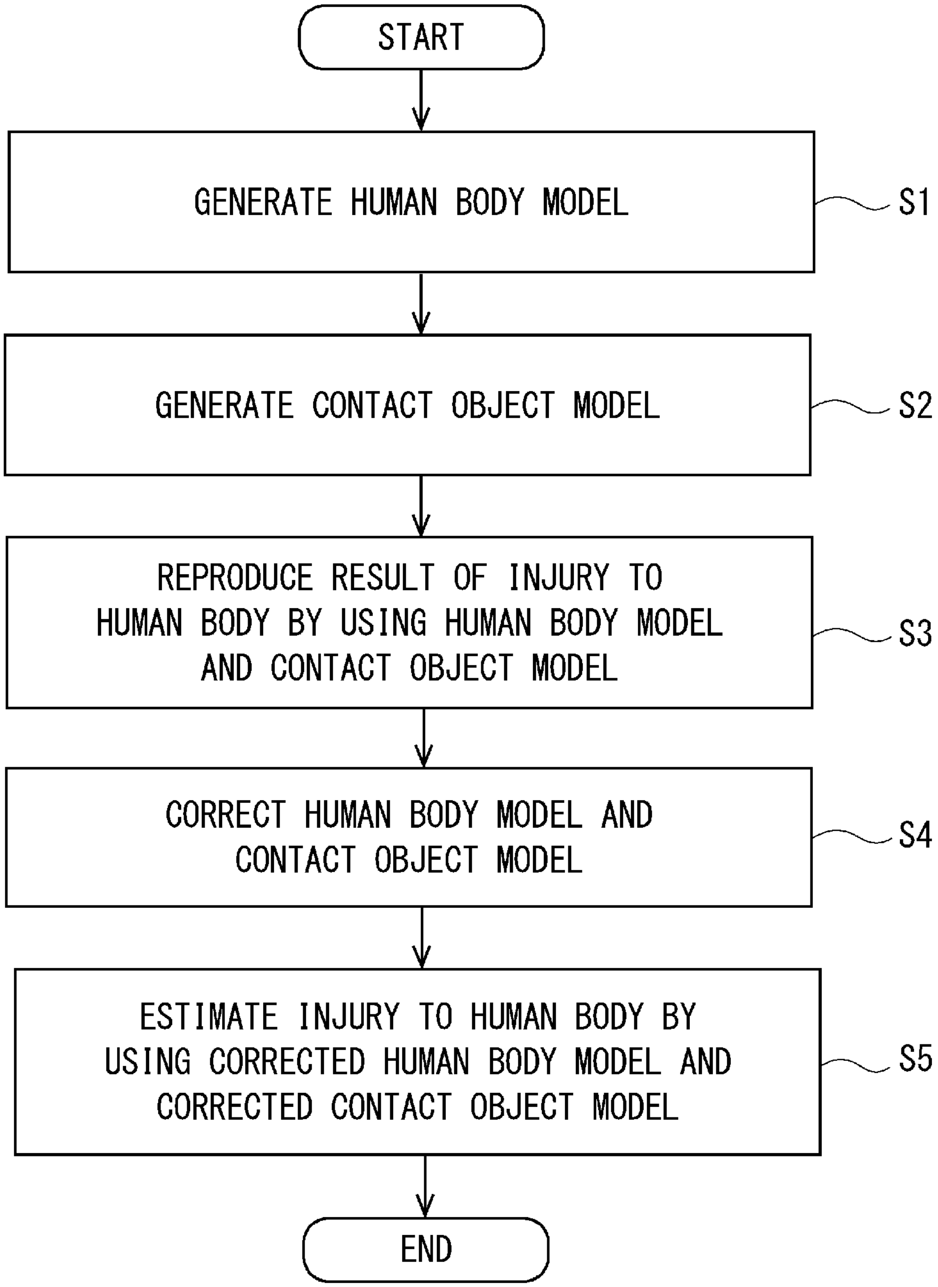
FIG. 3 is a flowchart showing an injury estimation method according to the first embodiment.

Next, an injury estimation method according to the first embodiment will be described with reference to FIG. 3. FIG. 3 is a flowchart showing the injury estimation method according to the first embodiment. The injury estimation method according to the first embodiment is a method for estimating an injury to a human body by using the human body model and the contact object model.

The human body model is generated by using the human body information stored in the database that stores the human body information about a human body, the contact object information about contact objects, and injury information about an injury to the human body generated due to contact between the human body and the contact object in association with each other (Step S1). Next, the contact object model is generated by using the contact object information stored in the database (Step S2). The order of the Steps S1 and S2 may be reversed.

A result of an injury to the human body is reproduced by using the human body model and the contact object model (Step S3). Next, the human body model and the contact object model are corrected based on the injury information shown by the reproduced result of the injury to the human body and the injury information about the human body stored in the database (Step S4). After that, an injury to the human body is estimated by using the corrected human body model and the corrected contact object model (Step S5).

Steps S3 to S5 may be repeated. In the injury estimation method according to this embodiment, the precision of the human body model and the contact object model can be further improved by repeating Steps S3 to S5.

According to the injury estimation system 100 and the injury estimation method of this embodiment, an injury to a human body can be estimated in advance by using the human body model and the contact object model. Thus, safety measures can be taken in advance at a work site or the like, and thus the degree of the injury to the human body can be reduced. For example, the degree of the injury to the human body can be reduced by changing the protective equipment, changing the shape of the contact object, and re-examining the operation procedure in consideration of the injury to the human body estimated using the injury estimation system 100 and the injury estimation method according to this embodiment.

In the injury estimation system 100 and the injury estimation method according to this embodiment, it may be possible to propose a safety measure such as a change to protective equipment or a change in the shape of a contact object which can improve safety according to the estimated injury to the human body.

Figure 4:
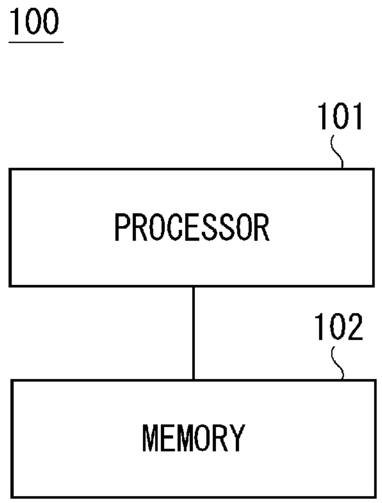
FIG. 4 is a block diagram showing a hardware configuration example of the injury estimation system according to the first embodiment.

A hardware configuration example of a control apparatus of the injury estimation system 100 according to the first embodiment will be described with reference to FIG. 4. The control apparatus of the injury estimation system 100 includes a processor 101 and a memory 102. The processor 101 may be, for example, a microprocessor, a MPU (Micro Processing Unit), or a CPU (Central Processing Unit). The processor 101 may include a plurality of processors. The memory 102 is composed of a combination of a volatile memory and a non-volatile memory. The memory 102 may include a storage disposed separately from the processor 101. In this case, the processor 101 may access the memory 102 through an I/O interface (not shown).

Each of the apparatuses in the above-described embodiments is composed of hardware and/or software, and may be composed of one piece of hardware or software, or may be composed of a plurality of pieces of hardware or software. The function (processing) of each apparatus in the above-described embodiment may be implemented by a computer. For example, a program for performing an operation in the embodiment may be stored in the memory 102, and each function may be implemented by the processor 101 executing the program stored in the memory 102.

An injury estimation program according to this embodiment is for estimating an injury to a human body by using a human body model and a contact object model for causing a computer to execute: generating the human body model by using human body information stored in a database configured to store, in association with each other, the human body information about a human body, contact object information about a contact object, and injury information about an injury to the human body generated in contact between the human body and the contact object; generating the contact object model by using the contact object information stored in the database; reproducing a result of an injury to the human body by using the human body model and the contact object model; correcting the human body model and the contact object model based on the reproduced injury information indicated by the result of the injury to the human body and the injury information about the human body stored in the database; and estimating the injury to the human body by using the corrected human body model and the corrected contact object model.

The program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. An injury estimation system for estimating an injury to a human body by using a human body model and a contact object model, the injury estimation system comprising:

a database configured to store, in association with each other, human body information about the human body, contact object information about a contact object, and injury information about an injury to the human body generated in contact between the human body and the contact object;

at least one memory storing instructions; and at least one processor, that when executing the instructions is configured to: generate the human body model by using the human body information stored in the database;

generate the contact object model by using the contact object information stored in the database;

reproduce a result of an injury to the human body by using the human body model and the contact object model;

correct the human body model by changing parameters of the human body model and correct the contact object model by changing parameters of the contact object model when the reproduced injury information indicated by the result of the injury to the human body is different from the injury information about the human body stored in the database; and estimate the injury to the human body by bringing the corrected human body model into contact with the corrected contact object model under a specified contact condition, wherein the human body model includes a living body model related to a living body of a human and a protective equipment model related to protective equipment attached to the living body of the human.

2. The injury estimation system according to claim 1, wherein the living body model includes a parameter related to a frictional force in a surface layer of a hand of the human body, slipperiness in the surface layer of the hand of the human body, a fat amount of the hand of the human body, a muscle mass of the hand of the human body, or a bone of the hand of the human body.

3. The injury estimation system according to claim 1, wherein the contact object model includes a parameter related to a shape or a material property of the contact object.

4. The injury estimation system according to claim 1, wherein the injury information includes information about a shape, a contact area, or an amount of chamfer of a contact region of the human body which comes into contact with the contact object.

5. The injury estimation system according to claim 1, wherein an injury to the hand of the human body is estimated.

6. The injury estimation system according to claim 1, wherein the at least one processor, that when executing the instructions is configured to:

estimate the injury to the human body when the human body comes into contact with the contact object in an area of 1 $cm^2$ or more on a surface of the human body using the corrected human body model and the corrected contact object model.

7. The injury estimation system according to claim 1, wherein the at least one processor, that when executing the instructions is configured to:

estimate the injury to the human body, in a simulated virtual space, by bringing the corrected human body model into contact with the corrected contact object model under a specified contact condition, and display, on a display, the injury to the human body as a three-dimensional map.

* * * * *